（12）United States Patent
Wardlaw

(10) Patent No.: US 6,204,066 B1
(45) Date of Patent: Mar. 20, 2001

(54) RAPID METHOD FOR DETERMINING THE ERYTHROCYTE SEDIMENTATION RATE IN A SAMPLE OF ANTICOAGULATED WHOLE BLOOD

(75) Inventor: Stephen C. Wardlaw, Lyme, CT (US)

(73) Assignee: Robert A. Levine, Guilford, CT (US)

( * ) Notice: Subject to any disclaimer, the term of this patent is extended or adjusted under 35 U.S.C. 154(b) by 0 days.

(21) Appl. No.: 09/344,991

(22) Filed: Jun. 25, 1999

(51) Int. Cl.$^7$ .................................................. G01N 33/86
(52) U.S. Cl. .............................. 436/70; 436/69; 436/177; 422/73; 73/61.65
(58) Field of Search ................................ 436/63, 69, 70, 436/45, 177; 422/72, 73; 73/61.65

(56) References Cited

U.S. PATENT DOCUMENTS

| | | | |
|---|---|---|---|
| 3,824,841 | * 7/1974 | Bull | 73/61.4 |
| 4,558,947 | * 12/1985 | Wardlaw | 356/39 |
| 5,731,513 | * 3/1998 | Bull | 73/61.66 |
| 5,827,746 | * 10/1998 | Duic | 436/70 |
| 5,888,184 | * 3/1999 | Wardlaw | 494/37 |

FOREIGN PATENT DOCUMENTS 41 16 313 A1   11/1992  (DE) .
96/39618  * 12/1996  (WO) .
99/45363  *  9/1999  (WO) .

* cited by examiner

*Primary Examiner*—Maureen M. Wallenhorst
(74) *Attorney, Agent, or Firm*—William W. Jones

(57) ABSTRACT

A method for determining the sedimentation rate of erythrocytes (ESR) includes the steps of placing an anticoagulated sample of whole blood in a transparent capillary tube and subjecting the blood sample and the tube to centrifugation. The position of the erythrocyte/plasma interface in the blood sample is determined at known time intervals during centrifugation of the blood sample. A point during centrifugation wherein the position of the erythrocyte/plasma interface becomes non-linear relative to elapsed centrifugation time is determined; and the slope of successive non-linear interface positions which are observed at subsequent elapsed centrifugation times occurring between the aforesaid point, to the time of substantial completion of centrifugation of the sample, is calculated. A value which reflects the sedimentation rate of the sample, if the sedimentation rate measurement were performed under ambient gravity conditions, can be derived from the calculated slope and the Y intercept of the calculated slope, thereby arriving at a conventional gravity sedimentation rate value from the erythrocyte/plasma interface positions determined during centrifugation of the blood sample.

23 Claims, 2 Drawing Sheets

RAPID METHOD FOR DETERMINING THE ERYTHROCYTE SEDIMENTATION RATE IN A SAMPLE OF ANTICOAGULATED WHOLE BLOOD

TECHNICAL FIELD

This invention relates to a method for determining the erythrocyte, or red blood cell, sedimentation rate in a sample of anticoagulated whole blood which is contained in a transparent tube. More particularly, this invention relates to a method for rapidly determining the erythrocyte sedimentation rate from successive erythrocyte layer/plasma interface position readings taken at known time intervals during centrifugation of the blood sample in the tube.

BACKGROUND ART

The erythrocyte sedimentation rate (ESR) is a widely used test which can help determine if a patient has a condition which is causing sub-acute or chronic inflammation. It Is non-specific, but It is still very helpful, particularly in following the course of some inflammatory diseases. Some of the problems with the test are that it uses a relatively large amount of blood (about one-half ml or more); it normally requires at least sixty minutes to complete, and thus is somewhat impractical for immediate patient care; and it requires the operator to handle bloody equipment. Additionally, the test requires a relatively high degree of skill and care in setting it up if the results are to be trusted.

The Westergren ESR test, which is the "Gold Standard" reference method for the ESR, is performed by placing a diluted sample of anticoagulated blood in a tall, perfectly vertical tube and measuring how far the plasma/erythrocyte (P/E) interface has settled under the influence of gravity after sixty minutes. The test works because the proteins associated with inflammation, particularly fibrinogen, counteract the zeta potential of red blood cells, which is a negative surface charge on the erythrocytes that serves to repel the individual erythrocytes from each other and thus prolong erythrocyte sedimentation. When systemic inflammation is present, the fibrinogen content of the blood increases, and the erythrocytes tend to aggregate, and thereby decrease their surface-to-mass ratio, and thus increase their rate of sedimentation.

Various approaches to automation have been attempted, notably the use of electronic means to track the sedimentation of the erythrocytes and provide a result in less than the usual sixty minutes, but these methods require at least fifteen minutes, and their results do not correlate well with the "reference" ESR method, i.e., that of Westergren.

A centrifugal method for packing blood so as to determine the approximate ESR was invented by Brian S. Bull et al, and is described in U.S. Pat. No. 3,824,841. The Bull et al method is, however, undesirable since it requires a large amount of blood and subjects the clinician performing the test to the possibility of exposure to infectious aerosols.

Another centrifugal method for measuring the ESR has been proposed by James W. Winkelman et al and is described in International Patent Application No. WO 96/39618. The Winkelman et al technique solves many of the problems of previous ESR techniques in that it uses a smaller quantity of blood and provides results within a few minutes. The Winkelman et al method involves the centrifugation of a quantity of blood in a disc-shaped rotor chamber and the observance of position of the P/E interface as the blood cells pack under centrifugal force. The total time from the start of centrifugation to the cessation of movement of the interface is related to the ESR. This device also requires a modest amount of blood, and the results moderately correlate with the Westergren method.

It would be desirable to be able to perform a rapid ESR measurement using a conventional blood sample container, such as a capillary tube, or the like, so as to derive an ESR from a small amount of blood in a matter of minutes

DISCLOSURE OF THE INVENTION

The method of this invention indirectly measures the repulsion or zeta potential of the erythrocytes, which is the main contributor to the sedimentation rate. The erythrocytes are caused to settle gravimetrically in a discrete layer in a capillary tube under modest centrifugation, and the movement of the plasm/erythrocyte interface is mathematically analyzed to yield an ESR number which closely correlates to the ESR obtained by the method of Westergren.

I have observed that in an anticoagulated blood sample which is centrifuged in a capillary tube, the position of the red blood cell-plasma interface in the capillary tube descends in the capillary tube, over time, initially in a linear fashion until such time that the repulsion force zeta potential of the red blood cells becomes the controlling factor in the red blood cell layer compaction, after which the position of the red blood cell-plasma interface descends in the capillary tube in a non-linear fashion. Thus the red blood cell layer in a centrifuged sample of anticoagulated whole blood sample compacts in an initially linear fashion and in a subsequent non-linear fashion to substantial completion.

I have determined that the initial linear portion of the red blood cell layer compaction in a capillary tube is due to the patient's hematocrit, and the subsequent non-linear portion of the red blood cell layer compaction in a capillary tube is due primarily to the strength of the repulsion or zeta potential of the subject's red blood cells. Thus, the compaction of the red blood cell layer, over time, can be plotted as a curve having an initial linear portion and an subsequent non-linear portion.

The method of this invention involves the detection of the beginning of the non-linear portion of the red blood cell compaction curve; the determination of the slope of a mazthematically linearized transformation of the non-linear portion of the red blood cell compaction curve; and correction of the length of the packed red blood cells resulting from the linear hematocrit-related part of the curve. I have found that after the initial linear compaction of the red blood cell layer, there occurs a "knee" in the compaction curve wherein the curve becomes non-linear. The non-linear portion of the red cell compaction curve continues after occurrence of the knee to a theoretical point of ultimate erythrocyte compaction which would occur if the blood sample were centrifuged for an endless period of time.

This invention involves the linearization of the non-linear portion of the curve which follows the knee, and the determination of the slope of the linearized portion of the curve. The linearization step can be performed by mathematically transforming the non-linear portion of the curve to a linear representation by means of a hyperbolic or exponential fit of successive erythrocyte/plasma interface locations derived during centrifugation of the blood sample. The method also involves the determination of a corrected starting time for the red cell compaction which negates the initial linear portion of the red cell compaction curve. This corrected starting time, which I refer to in this description as "$t_c$", can typically be a time that is about midway between the elapsed time that the knee is formed, and the elapsed time that the erythrocyte compaction is substantially completed.

It is therefore an object of this invention to provide an ESR measurement within a few minutes after drawing a blood sample so that this useful diagnostic data will be available while the patient is still in the physician's office.

It is a further object of this invention to provide the ESR measurement results from a tiny quantity of blood, so that that a venipuncture may be avoided, although venous blood may also be used.

It is yet another object of this invention to provide ESR measurement results which closely match those obtained by the traditional Westergren method.

These and other objects and advantages of the invention will become more readily apparent from the following detailed description of a specific embodiment of the invention when taken in conjunction with the accompanying drawings, in which:

SPECIFIC EMBODIMENT OF THE INVENTION

Figures 1, 2:
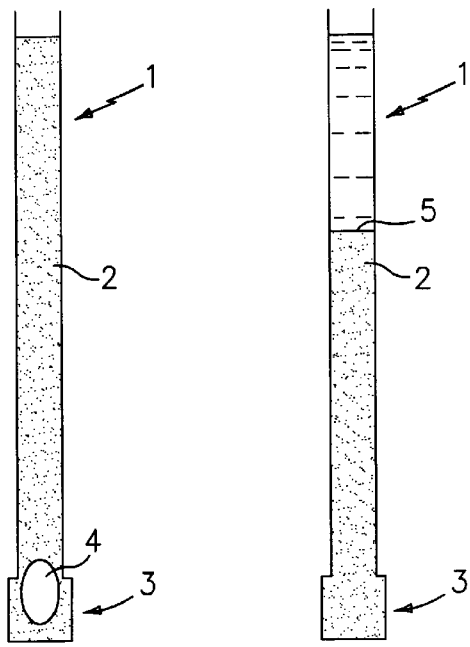
FIG. 1 is a schematic side elevational view of a capillary tube which is filled with anticoagulated blood ready for analysis.
FIG. 2 is a view similar to FIG. 1, but showing the capillary tube during centrifugation of the blood sample in the tube.

Referring now to the drawings, as shown in FIG. 1, a capillary tube 1 is prepared for the ESR analysis by filling the tube 1 with about seventy μl of whole blood 2 and sealing one end of the tube 1 with a closure 3. When the sample is drawn from a fingerstick rather than from an anticoagulated sample, an effective amount of an anticoagulant such as EDTA may be dried in the tube 1 to prevent coagulation. In order to ensure mixing of the sample, it is preferable to include at least a small air bubble 4 at the bottom of the tube, or use a small piece of foam, which will act like a bubble and float to the top of the tube when centrifugation begins. An air bubble is easily trapped by filling the tube from the top and allowing the blood sample 2 to partially run down the tube 1 before applying the closure 3. A more reliable method would be to coat the inside of the tube 1 with a hydrophobic material, such as silicone, at a position where it is desired that the blood flow stop. Thus, the blood moving down the tube during filling can be halted at a precise location in the tube 1 and can be made to produce a bubble 4 of the desired size. The mixer 4 acts to disrupt any red blood cell rouleaux which spontaneously form in blood in a quiescent state between the time the tube 1 is filled and the time centrifugation of the sample begins. If these rouleaux formations are not disrupted prior to the measurement process, inaccurate results may be obtained.

The filled tube 1 is centrifuged in an instrument which repetitively measures the position of the P/E interface 5 in relation to the closure 3, such as the QBC-STAR instrument sold by Becton Dickinson and Company. Such an instrument is described in U.S. Pat. No. 5,889,584, granted Mar. 30, 1999. The aforesaid instrument will be properly programmed so as to perform the sedimentation rate measurements in accordance with the precepts of this invention. It will therefore be appreciated that the instrument will include a computer that should preferably be programmed to perform the necessary mathematical calculations described hereinafter. The tube 1 is preferably centrifuged at about 4,000 RPM, although higher or lower speeds may be used. The centrifugation is continued until the computer associated with the instrument has gathered sufficient data to perform the calculations to complete the test.

Figure 3:
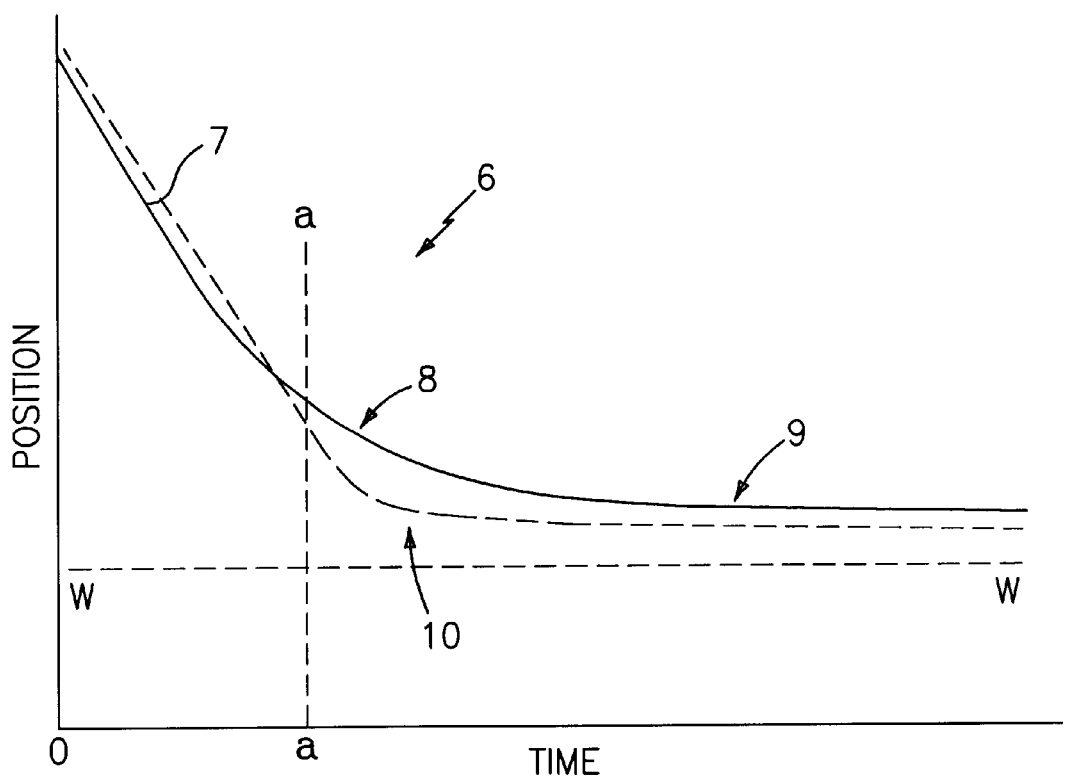
FIG. 3 is a plot of various positions of the plasma/erythrocyte interface in the blood sample during centrifugation as compared to elapsed centrifugation time in a blood sample with a normal ESR (solid line); and showing various interface positions in a blood sample with a high ESR (broken line)

FIG. 3 shows the position in a solid line of the P/E interface as plotted against elapsed centrifugation time in a blood sample which is known to have a normal ESR. If the method of Winkelman et al were to be applied to this data, the measurement would be the total elapsed time from the start of centrifugation to the cessation of movement of the P/E interface 5. I have found that applying the total elapsed time method suggested by Winkelman et al to the analysis of blood in a capillary tube will not produce dependable results. Apparently, the fluid dynamics in a capillary tube and the disc-shaped centrifuge chamber used by Winkelman et al are very different.

As seen in FIG. 3, in the trace of the declining P/E interface position versus elapsed centrifugation time, which trace is generally denoted by the numeral 6, there is an initial essentially linear declination 7 in the position of the P/E interface when the blood sample is centrifuged in a capillary tube 1. The slope of the initial linear declination 7, and therefore the elapsed time required for the initial linear declination to terminate, is determined solely by the hematocrit in the blood sample. This was determined by correlating the values of the initial linear declination with the hematocrit of a series of samples, and observing that this correlation was nearly perfect; while the correlation of the initial linear declination with other sample parameters, particularly the ESR, was essentially random. Therefore, if the "total centrifugation time" approach of the Winkelman et al procedure were applied to my technique, a large error could be introduced due to differences in the hematocrits of the various blood samples being tested. After the initial linear declination slope 7, there is a flattened "knee" 8 in the trace 6, and a subsequent exponentially declining slope 9, the latter of which continues until the erythrocyte layer compaction is essentially completed.

It is the exponentially declining slope 9 portion of the trace 6 that, when properly analyzed, contains information which is related to the zeta potential, and thus the ESR. It is theorized that, as the erythrocytes pack and the inter-cellular erythrocyte distances decrease, the effect of the repelling zeta potential acts like "springs", keeping the cells separated and slowing their packing. In a sample with a reduced zeta potential, that is, one with a high ESR, this repulsive force is diminished or lacking, and the cells quickly approximate. This is shown in broken line trace 10 in FIG. 3, which is representative of a sample with a high ESR, where the exponential curve flattens out quickly following the initial linear portion because of the diminution or lack of the repelling zeta potential.

The analysis of the compaction of the P/E interface involves three basic steps:
  a) determining the start of the exponential portion of the curve;
  b) determining the slope of an essentially linearized transformation of a portion of the exponential portion of the curve; and
  c) correcting for the packed length of the erythrocytes.

The following is an example of a typical calculation after the sample has been centrifuged for about five minutes, or until compaction of the erythrocytes is sufficient for accurate calculations of the slope of the exponential essentially linear transformation of the non-linear portion of the curve.

The end of the linear phase of compaction and the beginning of the exponential phase lies between the beginning of centrifugation and the "knee" of the curve 6, which lies approximately at point 11. This knee can readily be determined by mathematically calculating the second derivative of the curve 6, and then locating the highest point of the second derivative, or by other well-known mathematical operations. Once the time at which the knee point 11 occurs has been located, this information is used to calculate the exact start of the exponential portion of the curve 6. This calculation may be done by performing a least-squares fit of the value $1/(t-t_c)$, wherein "t" is the actual centrifugation time and "$t_c$" is a correction time, which is initially set to the value at the point 11, and the interface position value at that point in time. The fit is calculated for all values wherein $(t-t_c)$ is greater than zero. A chi-square value for that fit is then determined and saved. Next, the correction time is decremented by some value, typically about five seconds, and the aforesaid calculations are repeated. The chi-square value of the first fit is compared to the chi-square value of the second fit, and if the value of the second fit is lower, thereby indicating a better linearized fit, $t_c$ is decremented again, and the process is continued until the lowest chi-squared value is obtained. At this point, the fit of the linearization of the exponential part of the curve is optimized, or stated another way, the "straightness" of the linearization is maximized.

Figure 4:
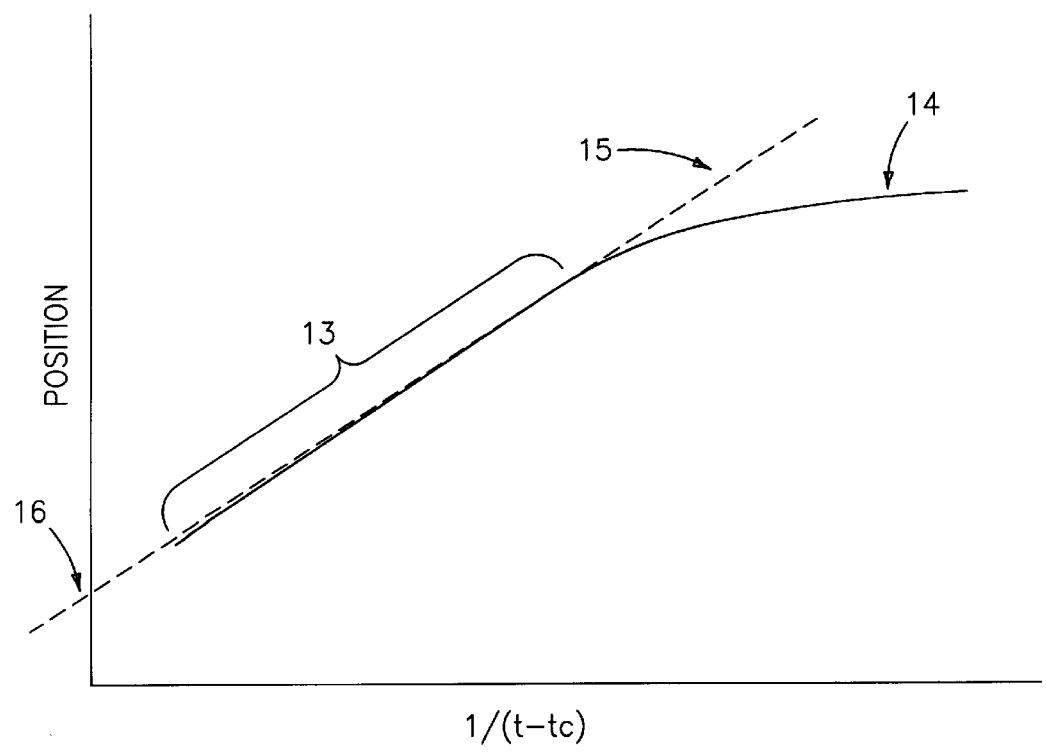
FIG. 4 shows the same data as In FIG. 3, but plotted on a time-corrected hyperbolic scale.

FIG. 4 shows a typical plot in hyperbolic space of the fitted data 15, and the actual curve 14, wherein a best fit is determined over the region 13 of curve 14 to produce a fitted line 15. In this graph, the Y axis point of intercept 16 with the fitted line plot 15 is indicative of the position of the erythrocyte-plasma interface 5 after an infinite period of centrifugation of the blood sample. In other words, the Y axis intercept 16 with the fitted line 15 predicts what the terminal interface position ($i_p$) would be if the sample were spun forever. A mathematical function, such as the slope (sl) of the linearized line 15 is then determined, which slope sl represents the magnitude of the erythrocyte zeta potential for a particular length of packed red blood cells.

To isolate the effect of the zeta potential, which is the desired measurement, it is required that the slope of the linearized line 15 be corrected for the length of the packed red blood cell column $i_p$. This correction is $i_p/sl$, which is directly proportional to the Westergren sedimentation rate. This numerical value $i_p/sl$ may be used as is, with its own normal and abnormal ranges for patient care, but it is usually more desirable that the number be numerically equal to the Westergren sedimentation rate value of millimeters per hour, with which practitioners are most comfortable. To convert the centrifugal sedimentation value to the Westergren value, one uses the formula: $V_W = k_1 + (k_2 \cdot V_c)$; wherein $V_W$ is Westergren units; $V_c$ is the value calculated using the method of this invention; $k_1$ is an intercept constant; and $k_2$ is a slope constant. The values $k_1$ and $k_2$ are easily found by analyzing a series of samples with varying sedimentation rates by both the Westergren method and the method of this invention, and performing a least-squares fit on the resultant data. The constants $k_1$ and $k_2$ are respectively the intercept and slope constants of the least squares fit.

To better illustrate how the calculations are performed, the following data, taken from two patients, one with a normal ESR and one with a high ESR are shown. For clarity's sake, the data is shown in thirty second intervals, while, in actuality, the data was recorded in five second intervals. The sets of data were collected as the samples were centrifuged. The data consist of the red blood cell-plasma interface positions in the sample tube versus the elapsed times of centrifugation. The times are in minutes, and the interface positions are in instrument units, which, in this case are equal to about 0.005 inch. The following is a table of the aforesaid readings during centrifugation.

| Elapsed time | Patient with a normal ESR Interface position | Patient with a high ESR Interface position |
| --- | --- | --- |
| 0.0 | 2951 | 2917 |
| 0.5 | 2781 | 2619 |
| 1.0 | 2500 | 2191 |
| 1.5 | 2185 | 1764 |
| 2.0 | 1867 | 1463 |
| 2.5 | 1646 | 1368 |
| 3.0 | 1535 | 1330 |
| 3.5 | 1477 | 1311 |
| 4.0 | 1439 | 1299 |
| 4.5 | 1413 | 1291 |
| 5.0 | 1390 | 1284 |

Next, the value of $t_c$ is calculated for each sample. The starting value of $t_c$ is set a zero, and the $t_c$ value is incremented 0.05 minutes for each iteration. The operation is complete when the chi-squared value is minimized. The chi-squared value was determined by performing a least squares regression on the data pairs, $1/(t-t_c)$, and then comparing the fitted curve to the actual data over the range of $(t-t_c)>0$; and $(5.0 \text{ min.} - t_c)$. Once again, not all of the iterations are described below.

| Patient with a normal ESR | | Patient with a high ESR | |
| --- | --- | --- | --- |
| $t_c$ | chi-square | $t_c$ | chi-square |
| 0 | 9394 | | 8983 |
| .05 | 8960 | | 8693 |
| .10 | 8522 | | 8396 |
| 1.20 | 221 | 1.30 | 76 |
| 1.25 | 208 | 1.35 | 57 |
| 1.30 | 295 | 1.40 | 216 |

It will be noted from the above data that the optimum, or minimal, $t_c$ for the normal ESR is 1.25, and that the optimum, or minimal $t_c$ for the high ESR is 1.35.

Once the optimum $t_c$ is determined, the Y-intercept, which is the predicted ultimate compaction of the red blood cell layer of the regression using the optimum $t_c$ is calculated. In the examples noted, the Y-intercept for the normal ESR is 1259, and the Y-intercept for the high ESR is 1244. The slopes, i.,e., $\Delta Y/\Delta X$, of the two regressions are then determined, the slope for the normal ESR being 502, and the slope for the high ESR being 148. The value of the red blood cell Y-intercept divided by the slope for each ESR is then calculated, the values for the two examples being $1259/502 = 2.5$ for the normal ESR, and $1244/148 = 8.4$ for the high ESR. These values, 2.5 and 8.4 are the ESR results in instrument units for the specific set of conditions under which the tests were performed. If the centrifuge speed, the centrifuge radius, the capillary tube diameter, and the like constants are changed, the results will be numerically different, but the same relative differences will be seen between the two samples.

It is preferable to express the results of the kinetic measurement of the ESR described above in units with which a clinician is familiar, which is in units of mm/hr. In order to obtain the empirical data need to perform the conversion, a series of different blood samples were tested using the method of this invention performed under the same operating conditions, i.e., same centrifuge speed, same centrifuge radius, etc., and using the standard Westergren reference method for each sample. A regression analysis was performed on the data pairs, and the slope and intercept values of this "standardizing" set of samples were used to scale the results obtained using the method of this invention. This was done using blood samples from thirty different subjects, and the following values were obtained: slope=10; intercept=−17. Converting the instrument values described above into Westergren values we have 2.5×10−17=8 mm/hr for the normal ESR sample; and 8.4×10−17=67 mm/hr for the high ESR sample. The actual Westergren results for the two samples were 7 mm/hr for the normal ESR sample; and 60 mm/hr for the high ESR sample. It is noted that the correlation between the standard Westergren method and the kinetic method of this invention is quite acceptable.

It will be readily appreciated that the measurement of the ESR which is performed kinetically while the blood sample is being centrifuged allows the measurement to be performed in a much shorter time than the traditional method, and provides equivalent results. The measurement can be provided in instrument units or it can be converted to the traditional mm/hr units of the Westergren method. The instrument which is performing the method will be operated by a computer processor which will use the sensed data from the centrifuged blood sample and perform the necessary calculations to derive the ESR readings. The blood sample from which the ESR is derived can be either venous blood or capillary blood. The method of this invention thus allows, for the first time, the use of a blood sample obtained from a finger stick to measure the ESR of a patient. The time necessary for performing an ESR test by the method of this invention is never longer than about six minutes, as compared to a time period measured in hours for the traditional Westergren ESR procedure.

Since many changes and variations of the disclosed embodiment of the invention may be made without departing from the inventive concept, it is not intended to limit the invention otherwise than as required by the appended claims.

What is claimed is:

1. A method for determining the magnitude of intercellular erythrocyte repulsion in a sample of anticoagulated whole blood, said method comprising:
   a) the step of placing the anticoagulated sample of whole blood in a transparent capillary tube;
   b) the step of centrifuging said blood sample in said capillary tube for a period of time;
   c) the step of recording positions of an erythrocyte/plasma interface in said capillary tube at known time intervals during said centrifuging step so as to establish a time-related red cell layer compaction curve for the erythrocytes in said blood sample, said compaction curve having an initial approximately linear portion and a subsequent non-linear portion;
   d) the step of determining a point in time in said compaction curve wherein the position of said compacting erythrocyte/plasma interface changes from said approximately linear portion to said non-linear portion; and
   e) the step of calculating a mathematical function for a plurality of the erythrocyte/plasma interface positions occurring in said non-linear portion of said curve, said function being operative to determine the magnitude of intercellular erythrocyte repulsion in said blood sample.

2. A method for determining the magnitude of intercellular erythrocyte repulsion in a sample of anticoagulated whole blood, said method comprising:
   a) the step of placing the anticoagulated sample of whole blood in a transparent capillary tube;
   b) the step of centrifuging said blood sample in said capillary tube for a period of time;
   c) the step of recording successive positions of an erythrocyte/plasma interface in said capillary tube at successive known time intervals during said centrifuging step so as to establish a time-related red cell layer compaction curve for the erythrocytes in said blood sample, said compaction curve having an essentially linear portion and a non-linear portion;
   d) the step of selecting a segment of said compaction curve which lies in said non-linear portion of said compaction curve; and
   e) the step of determining a mathematical function for said selected segment of said compaction curve in relation to a known elapsed time period, where said function of said selected segment is representative of the magnitude of intercellular erythrocyte repulsion in said blood sample.

3. A method for determining the magnitude of intercellular erythrocyte repulsion in a sample of anticoagulated whole blood, said method comprising:
   a) the step of placing the anticoagulated sample of whole blood in a transparent capillary tube;
   b) the step of centrifuging said blood sample in said capillary tube for a period of time;
   c) the step of recording positions of an erythrocyte/plasma interface in said capillary tube at known time intervals during said centrifuging step so as to define a non-linear time-related red cell layer compaction curve for the erythrocytes in said blood sample; and
   d) the steps of essentially linearizing a plurality of the erythrocyte/plasma interface positions occurring in said curve during a known time span, and calculating a slope for said linearized positions so as to determine the magnitude of intercellular erythrocyte repulsion in said blood sample.

4. The method of claim 3 further comprising the step of determining a Y intercept for said slope.

5. The method of claim 3 further comprising the step of providing a blood sample mixing component in the capillary tube.

6. The method of claim 5 wherein said blood sample mixing component is something which is lighter than plasma and can rise through the whole blood sample during said centrifuging step.

7. The method of claim 3 wherein said centrifuging step lasts no longer than about six minutes.

8. A method for determining the magnitude of intercellular erythrocyte repulsion in a sample of anticoagulated whole blood, said method comprising:
   a) the step of placing the anticoagulated sample of whole blood in a transparent capillary tube;
   b) the step of centrifuging said blood sample in said capillary tube for a period of time;
   c) the step of recording positions of an erythrocyte/plasma interface in said capillary tube at known time intervals during said centrifuging step so as to establish a time-related red cell layer compaction curve for the erythrocytes in said blood sample which curve has an initial linear portion and a subsequent non-linear portion; and d) the step of calculating a slope (sl) of mathematically essentially linearized erythrocyte/plasma interface positions occurring in said non-linear portion of said curve during a known time span so as to determine the magnitude of intercellular erythrocyte repulsion in said blood sample.

9. The method of claim 8 wherein said step of calculating said slope includes the step of negating the time period during the centrifugation of the sample during which said linear portion of said curve is formed.

10. The method of claim 9 wherein the slope of said linearized interface positions is optimized by performing a series of least squares fits of the values $1/(t-t_c)$, wherein t is a time of centrifugation of the sample and $t_c$ is a point in time during the centrifugation whereat said linear portion of said curve has been negated, said least squares fit values being obtained for a plurality of centrifugation times t; and determining chi-square values for each of said least squares fit values so as to obtain a lowest chi-square fit value.

11. The method of claim 10 further comprising the step of determining a Y intercepts for said slope thereby determining a length ($i_p$) for a packed erythrocyte layer which would occur if the blood sample were centrifuged forever.

12. The method of claim 11 further comprising the step of deriving a Y intercept-corrected value ($V_c$) for the measured erythrocyte repulsion magnitude by solving the equation: $V_c = i_p/sl$; $V_c$ being representative of a measured erythrocyte sedimentation rate in the blood sample.

13. The method of claim 12 further comprising the step of converting said measured erythrocyte sedimentation rate to Westergren sedimentation rate units.

14. The method of claim 13 wherein said converting step is accomplished by solving the equation: $V_W = k_1 + (k_2 \cdot V_c)$; wherein $V_W$ is the erythrocyte sedimentation rate expressed in Westergren units of mm/hr; $k_1$ is a calculated intercept constant; and $k_2$ is a calculated slope constant.

15. A method for determining an erythrocyte sedimentation rate ($V_c$) in a sample of anticoagulated whole blood, said method comprising:

a) the step of placing the anticoagulated sample of whole blood in a transparent capillary tube;

b) the step of centrifuging said blood sample in said capillary tube for a period of time;

c) the step of recording positions of an erythrocyte/plasma interface in said capillary tube at known time intervals during said centrifuging step so as to establish a time related red cell layer compaction curve for the erythrocytes in said blood sample which curve has an initial linear portion and a subsequent non-linear portion;

d) the step of calculating a slope (sl) of an essentially linearized mathematical transformation of a plurality of the erythrocyte/plasma interface positions which occur in said non-linear portion of said curve during a known time span;

e) the step of determining a Y intercept for said slope thereby determining a length ($i_p$) for a packed erythrocyte layer which would occur if the blood sample were centrifuged forever; and f) the step of deriving a $V_c$ for the blood sample by solving the equation: $V_c = i_p/sl$.

16. The method of claim 15 wherein said step of calculating said slope includes the step of negating the time period during the centrifugation of the sample during which said linear portion of said curve is formed.

17. The method of claim 15 wherein said mathematical transformation is a hyperbolic fit which is optimized by performing a series of least squares fits of the values $1/(t-t_c)$, wherein t is a total time of centrifugation of the sample and $t_c$ is a point in time during the centrifugation whereat said linear portion of said curve has been negated, said least squares fits being obtained for a plurality of centrifugation times t; and determining chi-square values for each of said least squares fit values so as to obtain a lowest chi-square fit value, at which point the fit of the linearized portion of the curve is optimized.

18. A method for determining a Westergren equivalent of an erythrocyte sedimentation rate ($V_c$) in a sample of anticoagulated whole blood, said method comprising:

a) the step of placing the anticoagulated sample of whole blood in a transparent capillary tube;

b) the step of centrifuging said blood sample in said capillary tube for a period of time;

c) the step of recording positions of an erythrocyte/plasma interface in said capillary tube at known time intervals during said centrifuging step so as to establish a time-related red cell layer compaction curve for the erythrocytes in said blood sample which curve has an initial linear portion and a subsequent non-linear portion;

d) the step of calculating a slope (sl) of an essentially linearized mathematical transformation of a plurality of the erythrocyte/plasma interface positions which occur in said non-linear portion of said curve during a known time span;

e) the step of determining a Y intercept for said slope thereby determining a length ($i_p$) for a packed erythrocyte layer which would occur if the blood sample were centrifuged forever;

f) the step of deriving a $V_c$ for the blood sample by solving the equation: $V_c = i_p/sl$; and g) the step of converting the derived $V_c$ to Westergren equivalent sedimentation rate units by solving the equation: $V_W = k_1 + (k_2 \cdot V_c)$; wherein $V_W$ is the erythrocyte sedimentation rate expressed in Westergren units of mm/hr; $k_1$ is a calculated intercept constant; and $k_2$ is a calculated slope constant.

19. The method of claim 18 wherein said step of calculating said slope includes the step of negating the time period during the centrifugation of the sample during which said linear portion of said curve is formed.

20. The method of claim 18 wherein said mathematical transformation is optimized by performing a series of least squares fits of the values $1/(t-t_c)$, wherein t is a total time of centrifugation of the sample and $t_c$ is a point in time during the centrifugation whereat said linear portion of said curve has been negated, said least squares fits being obtained for a plurality of centrifugation times t; and determining chi-square values for each of said least squares fit values so as to obtain a lowest chi-square fit value, at which point the fit of the linearized portion of the curve is optimized.

21. A method for determining the magnitude of intercellular erythrocyte repulsion in a sample of anticoagulated whole blood, said method comprising:

a) the step of placing the anticoagulated sample of whole blood in a transparent capillary tube;

b) the step of centrifuging said blood sample in said capillary tube for a period of time;

c) the step of recording positions of an erythrocyte/plasma interface in said capillary tube at known time intervals during said centrifuging step so as to establish a time-related red cell layer compaction curve for the erythrocytes in said blood sample, said compaction curve having an initial approximately linear portion and a subsequent non-linear portion;

d) the step of determining a point in time in said compaction curve wherein the position of said compacting erythrocyte,/plasma interface changes from said approximately linear portion to said non-linear portion; and e) the step of mathematically manipulating said non-linear portion of said compaction curve so as to derive indices which relate to the magnitude of intercellular erythrocyte repulsion in said blood sample.

22. A method for determining the magnitude of intercellular erythrocyte repulsion in a sample of anticoagulated whole blood, said method comprising:

a) the step of placing the anticoagulated sample of whole blood in a transparent capillary tube;

b) the step of centrifuging said blood sample in said capillary tube for a period of time;

c) the step of recording positions of an erythrocyte/plasma interface in said capillary tube at known time intervals during said centrifuging step so as to establish a time-related red cell layer compaction curve for the erythrocytes in said blood sample, said compaction curve having an initial approximately linear portion and a subsequent non-linear portion;

d) the step of determining a point in time in said compaction curve wherein successive positions of said compacting erythrocyte/plasma interface is non-linear; and e) the step of determining a slope of mathematically derived indices of a linearization of a plurality of erythrocyte/plasma interface positions which occur in said non-linear portion of said curve after said point in time, said slope being determinative of the magnitude of intercellular erythrocyte repulsion in said blood sample.

23. The method of claim 22 comprising the further step of mathematically optimizing said slope.

* * * * *